US012774313B2

(12) United States Patent
Kumar

(10) Patent No.: US 12,774,313 B2
(45) **Date of Patent: *Oct. 27, 2026**

(54) MODIFIED FOLLICLE-STIMULATING HORMONE AND METHODS OF USING THE SAME

(71) Applicant: The Regents of the University of Colorado, a body corporate, Denver, CO (US)

(72) Inventor: T. Rajendra Kumar, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 857 days.

This patent is subject to a terminal disclaimer.

(21) Appl. No.: 17/662,312

(22) Filed: May 6, 2022

(65) Prior Publication Data

US 2022/0281940 A1 Sep. 8, 2022

Related U.S. Application Data

(63) Continuation-in-part of application No. PCT/US2020/059382, filed on Nov. 6, 2020.

(60) Provisional application No. 62/931,402, filed on Nov. 6, 2019.

(51) Int. Cl.

| | |
|---|---|
| ***C07K 14/59*** | (2006.01) |
| ***A61K 38/00*** | (2006.01) |
| ***A61P 3/00*** | (2006.01) |
| ***A61P 5/06*** | (2006.01) |
| ***A61P 15/08*** | (2006.01) |

(52) U.S. Cl.

CPC ................ *C07K 14/59* (2013.01); *A61P 3/00* (2018.01); *A61P 5/06* (2018.01); *A61P 15/08* (2018.01); *A61K 38/00* (2013.01)

(58) Field of Classification Search

CPC .... C07K 14/59; A61P 3/00; A61P 5/06; A61P 15/08; A61K 38/00

See application file for complete search history.

(56) References Cited

U.S. PATENT DOCUMENTS

| | | | |
|---|---|---|---|
| 9,527,899 | B2 | 12/2016 | Goletz et al. |
| 2001/0007757 | A1 | 7/2001 | Boime et al. |
| 2004/0126838 | A1 | 7/2004 | Defrees et al. |
| 2007/0281883 | A1 | 12/2007 | Rosenfeld et al. |

FOREIGN PATENT DOCUMENTS

| | | | |
|---|---|---|---|
| EP | 2601210 | B1 | 11/2016 |
| EP | 3075744 | B1 | 12/2019 |
| WO | 2005020934 | A2 | 3/2005 |
| WO | 2010/094031 | A1 | 8/2010 |
| WO | 2012/017058 | A1 | 2/2012 |
| WO | 2013010840 | A2 | 1/2013 |
| WO | 2007141778 | A3 | 6/2014 |
| WO | 2021-092358 | A1 | 5/2021 |

OTHER PUBLICATIONS

Pang, Use of follicle-stimulating hormone for the treatment of female infertility—current concepts, Women's Health, 2005, 1, pp. 87-95.*

Follitropin beta chain, from https://www.ncbi.nlm.nih.gov/protein/1XWD_B?report=genbank&log$=protalign&blast_rank=1&RID=X7ZWKG7N016, 2024, pp. 1-2.*

Bousfield George R et al: "Hypo-glycosylated human follicle-stimulating hormone (hFSH21/18) is much more active in vitro than fully-glycosylated hFSH (hFSH24)", Molecular and Cellular Endocrinology, Elsevier Ireland Ltd, IE, vol. 382, No. 2, Dec. 1, 2013 (Dec. 1, 2013), pp. 989-997.

Wang Huizhen et al: "Evaluation of in vivo bioactivities of recombinant hypo—(FSH21/18) and fully—(FSH24) glycosylated human FSH glycoforms in Fshb null mice", Molecular and Cellular Endocrinology, Elsevier Ireland Ltd, IE, vol. 437, Aug. 22, 2016 (Aug. 22, 2016), pp. 224-236.

International Preliminary Report on Patentability; PCT/US2020/059382, Jan. 21, 2021, 10 pages.

Zaidi, et al., "FSH, bone mass, body fat, and biological aging," Endocrinology, 159, 10 (2018) pp. 3503-3514.

Oduwole et al., "Role of follicle-stimulating hormone in spermatogenesis," Frontiers in Endocrinology, 9 (2018), pp. 763.

Muyan et al., "Secretion of lutropin and follitropin from transfected GH3 cells: evidence for separate secretory pathways," Molecular Endocrinology, 8.12 (1994), pp. 1789-1797.

Flack et al., "Site-directed mutagenesis defines the individual roles of the glycosylation sites on follicle-stimulating hormone," Journal of Biological Chemistry, 269.19 (1994), pp. 14015-14020.

Notification of Transmittal of the International Search Report and the Written Opinion of the International Searching Authority, or the Declaration, PCT/US2020/059382, Jan. 21, 2021, 15 pages.

Notification of Transmittal of the International Search Report and the Written Opinion, PCT/US2023/066734, Aug. 31, 2023, 13 pages.

Wang H., et al. "A human FSHB transgene encoding the double N-glycosylation mutant (Asn7Δ Asn24Δ) FSHB 1 subunit fails to rescue Fshb null mice", Molecular and Cellular Endocrinology, vol. 426, Feb. 19, 2016 (Feb. 19, 2016}, pp. 113-124.

(Continued)

*Primary Examiner* — Li N Komatsu

(74) *Attorney, Agent, or Firm* — Stanek Lemon Crouse & Meeks, PA

(57) ABSTRACT

The present inventive concept is related to a modified follicle-stimulating hormone (FSH), in particular, a hypo-glycosylated form of FSH, as well as compositions and formulations including, nucleic acids encoding, cell lines expressing, and methods of using the hypo-glycosylated FSH as disclosed herein. These methods of use include methods of treating infertility, methods of inducing follicle growth and/or maturation, methods of inducing oocyte/egg growth and/or maturation, methods of stimulating sex steroid secretion, methods of treating or preventing bone density loss, and methods of treating or preventing fatty tissue accumulation.

14 Claims, 9 Drawing Sheets

Specification includes a Sequence Listing.

(56) References Cited

OTHER PUBLICATIONS

Bousfield, George R., et al. "Hypo-glycosylated human follicle-stimulating hormone (hFSH21/18) is much more active in vitro than fully-glycosylated hFSH (hFSH24)", Molecular and Cellular Endocrinology 382 (2014) 989-997.
Butnev, Viktor Y., et al. "Production, purification, and characterization of recombinant hFSH glycoforms for functional studies", Molecular and Cellular Endocrinology 405 (2015) 42-51.
Wang H., et al. "Evaluation of in vivo bioactivities of recombinant hypo—(FSH21/18) and fully (FSH24) glycosylated human FSH glycoforms in Fshb null mice)", Molecular and Cellular Endocrinology 437 (2016) 224-236.

* cited by examiner

SEQUENCE LISTING

```
<160> NUMBER OF SEQ ID NOS: 10

<210> SEQ ID NO 1
<211> LENGTH: 92
<212> TYPE: PRT
<213> ORGANISM: Homo sapiens
<220> FEATURE:
<221> NAME/KEY: SITE
<222> LOCATION: (52)..(52)
<223> OTHER INFORMATION: Glycosylation
<220> FEATURE:
<221> NAME/KEY: SITE
<222> LOCATION: (78)..(78)
<223> OTHER INFORMATION: Glycosylation

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90


<210> SEQ ID NO 2
<211> LENGTH: 111
<212> TYPE: PRT
<213> ORGANISM: Homo sapiens
<220> FEATURE:
<221> NAME/KEY: SITE
<222> LOCATION: (7)..(7)
<223> OTHER INFORMATION: Glycosylation
<220> FEATURE:
<221> NAME/KEY: SITE
<222> LOCATION: (24)..(24)
<223> OTHER INFORMATION: Glycosylation

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
```

```
                85                  90                  95

Arg Gly Leu Gly Pro Ser Tyr Cys Ser Phe Gly Glu Met Lys Glu
            100                 105                 110


<210> SEQ ID NO 3
<211> LENGTH: 111
<212> TYPE: PRT
<213> ORGANISM: Artificial
<220> FEATURE:
<223> OTHER INFORMATION: N24A recombinant FSH-beta subunit sequence
<220> FEATURE:
<221> NAME/KEY: SITE
<222> LOCATION: (7)..(7)
<223> OTHER INFORMATION: Glycosylation

<400> SEQUENCE: 3

Asn Ser Cys Glu Leu Thr Asn Ile Thr Ile Ala Ile Glu Lys Glu Glu
1               5                   10                  15

Cys Arg Phe Cys Ile Ser Ile Ala Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110


<210> SEQ ID NO 4
<211> LENGTH: 111
<212> TYPE: PRT
<213> ORGANISM: Artificial
<220> FEATURE:
<223> OTHER INFORMATION: N24Q recombinant FSH-beta subunit sequence
<220> FEATURE:
<221> NAME/KEY: SITE
<222> LOCATION: (7)..(7)
<223> OTHER INFORMATION: Glycosylation

<400> SEQUENCE: 4

Asn Ser Cys Glu Leu Thr Asn Ile Thr Ile Ala Ile Glu Lys Glu Glu
1               5                   10                  15

Cys Arg Phe Cys Ile Ser Ile Gln Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110


<210> SEQ ID NO 5
<211> LENGTH: 390
<212> TYPE: DNA
```

```
<213> ORGANISM: Artificial
<220> FEATURE:
<223> OTHER INFORMATION: N24Q recombinant FSH-beta subunit CDS

<400> SEQUENCE: 5

atgaagacac tccagttttt cttccttttc tgttgctgga aagcaatctg ctgcaatagc     60

tgtgagctga ccaacatcac cattgcaata gagaaagaag aatgtcgttt ctgcataagc    120

atccagacca cttggtgtgc tggctactgc tacaccaggg atctggtgta taaggaccca    180

gccaggccca aaatccagaa aacatgtacc ttcaaggaac tggtatacga aacagtgaga    240

gtgcccggct gtgctcacca tgcagattcc ttgtatacat acccagtggc cacccagtgt    300

cactgtggca agtgtgacag cgacagcact gattgtactg tgcgaggcct ggggcccagc    360

tactgctcct ttggtgaaat gaaagaataa                                      390


<210> SEQ ID NO 6
<211> LENGTH: 333
<212> TYPE: DNA
<213> ORGANISM: Artificial
<220> FEATURE:
<223> OTHER INFORMATION: N24Q mature recombinant FSH-beta subunit CDS

<400> SEQUENCE: 6

aatagctgtg agctgaccaa catcaccatt gcaatagaga aagaagaatg tcgtttctgc     60

ataagcatcc agaccacttg gtgtgctggc tactgctaca ccagggatct ggtgtataag    120

gacccagcca ggcccaaaat ccagaaaaca tgtaccttca aggaactggt atacgaaaca    180

gtgagagtgc ccggctgtgc tcaccatgca gattccttgt atacataccc agtggccacc    240

cagtgtcact gtggcaagtg tgacagcgac agcactgatt gtactgtgcg aggcctgggg    300

cccagctact gctcctttgg tgaaatgaaa gaa                                  333


<210> SEQ ID NO 7
<211> LENGTH: 111
<212> TYPE: PRT
<213> ORGANISM: Artificial
<220> FEATURE:
<223> OTHER INFORMATION: N7A recombinant FSH-beta subunit sequence
<220> FEATURE:
<221> NAME/KEY: SITE
<222> LOCATION: (24)..(24)
<223> OTHER INFORMATION: Glycosylation

<400> SEQUENCE: 7

Asn Ser Cys Glu Leu Thr Ala Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110


<210> SEQ ID NO 8
```

```
<211> LENGTH: 111
<212> TYPE: PRT
<213> ORGANISM: Artificial
<220> FEATURE:
<223> OTHER INFORMATION: N7Q recombinant FSH-beta subunit sequence
<220> FEATURE:
<221> NAME/KEY: SITE
<222> LOCATION: (24)..(24)
<223> OTHER INFORMATION: Glycosylation

<400> SEQUENCE: 8

Asn Ser Cys Glu Leu Thr Gln Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110


<210> SEQ ID NO 9
<211> LENGTH: 390
<212> TYPE: DNA
<213> ORGANISM: Artificial
<220> FEATURE:
<223> OTHER INFORMATION: N7Q recombinant FSH-beta subunit CDS

<400> SEQUENCE: 9

atgaagacac tccagttttt cttccttttc tgttgctgga aagcaatctg ctgcaatagc      60

tgtgagctga cccagatcac cattgcaata gagaaagaag aatgtcgttt ctgcataagc     120

atcaacacca cttggtgtgc tggctactgc tacaccaggg atctggtgta taaggaccca     180

gccaggccca aaatccagaa aacatgtacc ttcaaggaac tggtatacga aacagtgaga     240

gtgcccggct gtgctcacca tgcagattcc ttgtatacat acccagtggc cacccagtgt     300

cactgtggca agtgtgacag cgacagcact gattgtactg tgcgaggcct ggggcccagc     360

tactgctcct ttggtgaaat gaaagaataa                                      390


<210> SEQ ID NO 10
<211> LENGTH: 333
<212> TYPE: DNA
<213> ORGANISM: Artificial
<220> FEATURE:
<223> OTHER INFORMATION: N7Q mature recombinant FSH-beta subunit CDS

<400> SEQUENCE: 10

aatagctgtg agctgaccca gatcaccatt gcaatagaga aagaagaatg tcgtttctgc      60

ataagcatca acaccacttg gtgtgctggc tactgctaca ccagggatct ggtgtataag     120

gacccagcca ggcccaaaat ccagaaaaca tgtaccttca aggaactggt atacgaaaca     180

gtgagagtgc ccggctgtgc tcaccatgca gattccttgt atacataccc agtggccacc     240

cagtgtcact gtggcaagtg tgacagcgac agcactgatt gtactgtgcg aggcctgggg     300

cccagctact gctcctttgg tgaaatgaaa gaa                                  333
```

MODIFIED FOLLICLE-STIMULATING HORMONE AND METHODS OF USING THE SAME

CROSS-REFERENCE TO RELATED APPLICATIONS

The present application is a bypass continuation-in-part application of PCT International Application No. PCT/US2020/059382, filed Nov. 6, 2020, which claims the benefit of U.S. Provisional Patent Application No. 62/931,402, filed Nov. 6, 2019, the disclosures of each of which are incorporated herein by reference in its entirety.

STATEMENT REGARDING FEDERAL SUPPORT

This invention was made with government support under grant number AG029531 awarded by National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 151077-00036IP_ST25.txt, 9,580 bytes in size, generated on Apr. 19, 2022 and filed via EFS-Web, is provided in lieu of a paper copy. The Sequence Listing is incorporated herein by reference into the specification for its disclosures.

FIELD OF THE INVENTION

The present invention relates to compositions including a recombinant form of Follicle-Stimulating Hormone (FSH), and methods of using the same for treating and/or preventing metabolic disorders such as: infertility; bone density loss; and/or fatty tissue accumulation.

BACKGROUND OF THE INVENTION

Follicle-Stimulating Hormone (FSH) is a pituitary-derived heterodimeric glycoprotein that is essential for female reproduction. It consists of a hormone-specific beta-subunit and an alpha-subunit that is common to other glycoprotein hormones in pituitary and placenta. Female mice or women lacking the FSH ligand as a result of mutations in the FSH beta-subunit are infertile, do not produce estrogen and their ovarian follicle development is arrested. For various genetic and other metabolic reasons, women do not also produce sufficient endogenous FSH and therefore require exogenous FSH supplementation for optimal ovarian follicle growth and estrogen production, a common practice in artificial reproductive technology (ART) induction protocols. However, the response rate in many women to recombinant FSH is very poor. Currently, clinical grade recombinant human FSH is expressed in Chinese Hamster Ovary (CHO) cells which have a different glycosylation machinery compared to that in pituitary.

The pituitary and serum levels of FSH change with aging and it was discovered that aging also changes the glycosylation signature specifically on the FSH beta-subunit resulting in different types of FSH glycoforms whose abundance is age-specific. It was discovered that during young and normal reproductive cycles, women produce more of a hypo-glycosylated FSH, designated $FSH^{21}$, whereas older women produce fully-glycosylated $FSH^{24}$. $FSH^{21}$ was found to be more biologically active, and binds FSH receptors on ovarian cells, and cell lines more effectively than $FSH^{24}$.

The commercial potential of recombinant human FSH products for use in ART protocols is enormous, exceeding 1.5 billion US dollars worldwide. As such, there is a need for improved products, such as improved FSH products, and methods of using such products in ART protocols and treatment of infertility. In addition, there is also presently a need for improved products, such as improved FSH products, and methods of using such products for treatment and prevention of bone density loss and fatty tissue accumulation.

SUMMARY OF THE INVENTION

The present inventive concept utilizes a hypo-glycosylated form of FSH, which provides the basis of the compositions and methods of the present inventive concept.

Thus, in an aspect of the inventive concept, provided is a recombinant Follicle-Stimulating Hormone (FSH) beta-subunit, wherein a glycosylation site on the FSH beta-subunit is substituted with an amino acid at which a glycan is not and/or cannot be attached.

In another aspect of the present inventive concept, provided is a recombinant Follicle-Stimulating Hormone (FSH) including an FSH alpha-subunit and an FSH beta-subunit, wherein a glycosylation site on the FSH beta-subunit is substituted with an amino acid at which a glycan is not and/or cannot be attached.

In another aspect of the present inventive concept, provided is a nucleic acid including a sequence encoding an FSH beta-subunit, wherein a glycosylation site on the FSH beta-subunit is substituted with an amino acid at which a glycan is not and/or cannot be attached.

In another aspect of the present inventive concept, provided is an expression vector comprising the nucleic acid including a sequence encoding an FSH beta-subunit, wherein a glycosylation site on the FSH beta-subunit is substituted with an amino acid at which a glycan is not and/or cannot be attached, and a heterologous promoter operably associated therewith.

In another aspect of the present inventive concept, provided is a cell line comprising an expression vector comprising the nucleic acid including a sequence encoding an FSH beta-subunit, wherein a glycosylation site on the FSH beta-subunit is substituted with an amino acid at which a glycan is not and/or cannot be attached, and a heterologous promoter operably associated therewith, and a cell line expressing an FSH beta-subunit or recombinant FSH including an FSH beta-subunit, wherein a glycosylation site on the FSH beta-subunit is substituted with an amino acid at which a glycan is not and/or cannot be attached.

In another aspect of the present inventive concept, provided is a pharmaceutical composition or formulation including an FSH beta-subunit or recombinant FSH including an FSH beta-subunit, wherein a glycosylation site on the FSH beta-subunit is substituted with an amino acid at which a glycan is not and/or cannot be attached, and a pharmaceutically acceptable carrier.

In another aspect of the present inventive concept, provided is a method of treating infertility in a subject including administration of a composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

In another aspect of the present inventive concept, provided is a method of inducing follicle growth and/or maturation comprising administration of a pharmaceutical composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

In another aspect of the present inventive concept, provided is a method of inducing oocyte/egg growth and/or maturation comprising administration of a pharmaceutical composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

In another aspect of the present inventive concept, provided is a method of stimulating secretion of a sex steroid including administering a therapeutically effective amount of a pharmaceutical composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

In another aspect of the present inventive concept, provided is a method of treating and/or preventing loss of bone density including administering a therapeutically effective amount of a composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

In another aspect of the present inventive concept, provided is a method of treating and/or preventing fatty tissue accumulation including administering a therapeutically effective amount of a composition or formulation including an FSH beta-subunit or recombinant FSH including an FSH beta-subunit, wherein a glycosylation site on the FSH beta-subunit is substituted with an amino acid at which a glycan is not and/or cannot be attached to a subject in need thereof.

The foregoing and other objects and aspects of the present inventive concept are explained in detail in the following set forth below.

DETAILED DESCRIPTION

Figure 1A:
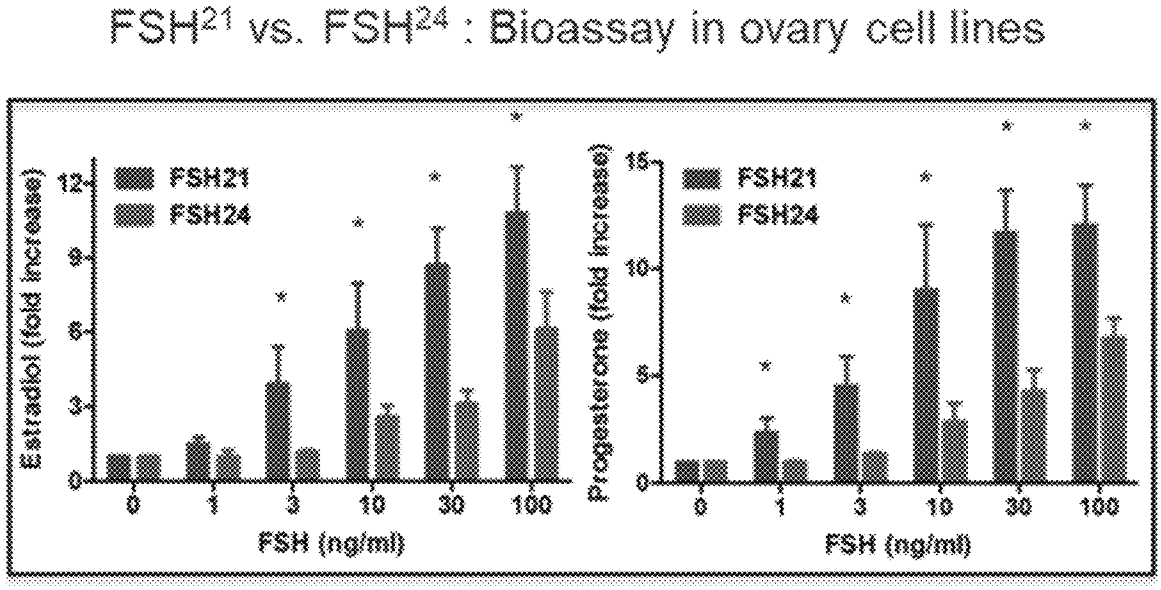
FIGS. 1A and 1B depict the comparison of recombinant $FSH^{21}$ and fully-glycosylated $FSH^{24}$ for induction of estradiol and progesterone production in vitro (FIG. 1A) and for induction of estradiol production in vivo (FIG. 1B) in Fshb knockout mice.

In the following detailed description, embodiments of the present invention are described in detail to enable practice of the invention. Although the invention is described with reference to these specific embodiments, it should be appreciated that the invention can be embodied in different forms and should not be construed as limited to the embodiments set forth herein. Rather, these embodiments are provided so that this disclosure will be thorough and complete, and will fully convey the scope of the invention to those skilled in the art. All publications cited herein are incorporated by reference in their entireties for their teachings.

The invention includes numerous alternatives, modifications, and equivalents as will become apparent from consideration of the following detailed description.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Additionally, as used herein, the term "and/or" includes any and all combinations of one or more of the associated listed items and may be abbreviated as "/".

Unless otherwise defined, all technical terms used herein have the same meaning as commonly understood by one of ordinary skill in the art to which this disclosure belongs.

As used herein, the term "comprise," in addition to its regular meaning, may also include, and, in some embodiments, may specifically refer to the expressions "consist essentially of" and/or "consist of." Thus, the expression "comprise" can also refer to embodiments, wherein that which is claimed "comprises" specifically listed elements does not include further elements, as well as embodiments wherein that which is claimed "comprises" specifically listed elements may and/or does encompass further elements, or encompass further elements that do not materially affect the basic and novel characteristic(s) of that which is claimed. For example, that which is claimed, such as an amino acid sequence, nucleic acid, nucleic acid sequence, peptide, protein, composition, formulation, cell line, vector, etc. "comprising" specifically listed elements also encompasses, for example, an amino acid sequence, nucleic acid, nucleic acid sequence, peptide, protein, composition, formulation, cell line, vector, etc. "consisting of," i.e., wherein that which is claimed does not include further elements, and, for example, an amino acid sequence, nucleic acid, nucleic acid sequence, peptide, protein, composition, formulation, cell line, vector, etc. "consisting essentially of," i.e., wherein that which is claimed may include further elements that do not materially affect the basic and novel characteristic(s) of that which is claimed.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) may refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

An "effective amount" or "therapeutically effective amount" may refer to an amount of a compound or composition of this invention that is sufficient to produce a desired effect, which can be a therapeutic and/or beneficial effect. The effective amount will vary with the age, general condition of the subject, the severity of the condition being treated, the particular agent administered, during the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, REMINGTON, THE SCIENCE AND PRACTICE OF PHARMACY (latest edition)).

A "nucleic acid" may include single-stranded and double-stranded nucleic acids and includes ribonucleic acids as well as deoxyribonucleic acids. It may include naturally occurring as well as synthetic nucleotides and can be naturally or synthetically modified.

A "vector" or "expression vector" may refer to and include any intermediary vehicle for a nucleic acid which enables said nucleic acid, for example, to be introduced into prokaryotic and/or eukaryotic host cells and, where appropriate, may be integrated into a genome of and/or expressed in the host cell. Vectors may thus be replicated and/or expressed in the host cells. A vector may include one or more selection markers for selecting host cells comprising the vector. Suitable selection markers include resistance genes which provide the host cell with a resistance IS, e.g. against a specific antibiotic. Further suitable selection markers include, for example, genes for enzymes such as DHFR or GS. Vectors enabling the expression of recombinant proteins including FSH of the inventive concept as described herein, as well as suitable expression cassettes and expression elements which enable the expression of a recombinant protein with high yield in a host cell are well known and are commercially available, and may include any that may be appreciated by one of skill in the art.

A "cell," "cells," and a "cell line" may be used interchangeably, and may refer to one or more cells and, in some embodiments, refer to mammalian cells, such as human cells. The term includes progeny of a cell or cell population. One of skill in the art will appreciate that "cells" include progeny of a single cell, and the progeny may not necessarily be completely identical (in morphology or of total DNA complement) to the original parent cell due to natural, accidental, or deliberate mutation and/or change. A "cell" may refer to isolated cells and/or cultivated cells which are not incorporated in a living human, non-human or animal body.

Compositions

Using Fshb null mice in a pharmacological assay, it has been shown that recombinant $FSH^{21}$ is more bioactive than $FSH^{24}$ in producing estradiol (Bousfield et al., 2014, *Mol. Cell. Endocrinol.* 382, 989-997; Wang et al., 2016, *Mol. Cell. Endocrinol.* 437, 224-236.). Interestingly, commercial preparations of recombinant FSH contain predominantly the $FSH^{24}$ form. Therefore, using $FSH^{21}$ may be more efficacious and desirable in ART protocols for better follicle induction and estradiol production, which are the 2 most important measures of success of these protocols.

Accordingly, the present inventive concept is based on a recombinant FSH for use in the treatment of metabolic disorders, for example, the treatment of infertility, the treatment and/or prevention of loss of bone density, and/or the treatment and/or prevention of fatty tissue accumulation in a subject in need thereof. "FSH" refers to follicle-stimulating hormone, a gonadotropin. In embodiments of the inventive concept, the FSH is human FSH, in particular human FSH, composed of an alpha-subunit and a beta-subunit. "Recombinant FSH," as used herein, may refer to FSH that is not naturally produced by a living, for example, human or animal body/subject, and then obtained from a sample derived therefrom, such as urine, blood or any other body fluid, waste, e.g., fecal matter, or tissue derived from the human or animal body/subject. In some embodiments, recombinant FSH may be obtained from cells which have been biotechnologically engineered, for example, cells which have been transformed or transfected with a nucleic acid encoding FSH or the alpha- or beta-subunits of FSH. According to some embodiments, recombinant FSH is obtained from human cells, mammalian cells, or non-mammalian, e.g., insect cells, comprising an exogenous nucleic and encoding for an FSH of the inventive concept. Respective exogenous nucleic acids can be introduced e.g. by using one or more expression vectors, for example, an expression vector including a nucleic acid encoding an FSH of the inventive concept as described herein, operably linked to a heterologous promoter, which can be introduced into the host cell e.g. via transfection. Methods for recombinantly producing expression vectors, cell lines including expression vectors, proteins and FSH are well known, and any recombinant method as would be appreciated by one of skill in the art may be used for producing expression vectors, cell lines including expression vectors, proteins and FSH of the present inventive concept. In some embodiments, the recombinant FSH of the inventive concept may be introduced into a host cell by genetic engineering using any method that would be appreciated by one of skill in the art.

As will be appreciated by one of skill in the art, "FSH" is a glycoprotein, i.e., a protein that has been modified by the addition of one or more oligosaccharides, including an alpha-subunit (FSH-$\alpha$) and a beta-subunit (FSH-$\beta$). "Glycosylation" is a process, typically within cells, by which oligosaccharides are covalently attached to, for example, a protein or polypeptide chain. With FSH, glycosylation takes place at particular asparagine (Asn) residues on the alpha-subunit and beta-subunit by N-glycosylation. Fully glycosylated human FSH (FSH$^{24}$) is a glycoprotein including oligosaccharides, also referred to as glycans or carbohydrates, attached at Asn-52 and Asn-78 of the mature form of FSH-α, and at Asn-7 and Asn-24 of the mature form of FSH-β.

In some embodiments of the present inventive concept, the recombinant FSH is a hypo-glycosylated form of FSH, i.e., an FSH that is not fully glycosylated. In some embodiments, the mature form of FSH-α has, and/or includes, an amino acid sequence as set forth in amino acids 25-116 (SEQ ID NO:1) of GenBank/NCBI Accession No. NP_000726.1 or AAH10957.1, encoded by GenBank/NCBI Accession No. CCDS5007.1, and the mature form of FSH-β has, and/or includes, an amino acid sequence as set forth in amino acids 19-129 (SEQ ID NO:2) of GenBank/NCBI Accession No. NP_000501.1 or AAA52476.1, encoded by GenBank/NCBI Accession No. CCDS 7868.1.

```
                                         (SEQ ID NO: 1)
APDVQDCPEC TLQENPFFSQ PGAPILQCMG CCFSRAYPTP

LRSKKTMLVQ KNVTSESTCC VAKSYNRVTV MGGFKVENHT

ACHCSTCYYH KS

                                         (SEQ ID NO: 2)
NSCELTNITI AIEKEECRFC ISINTTWCAG YCYTRDLVYK

DPARPKIQKT CTFKELVYET VRVPGCAHHA DSLYTYPVAT

QCHCGKCDSD STDCTVRGLG PSYCSFGEMK E.
```

In some embodiments, the recombinant FSH-α and FSH-β subunits of the inventive concept may have about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1 or SEQ ID NO:2, e.g., 1, 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid substitutions, additions and/or deletions on one or both subunits, so long as Asn-52 and Asn-78, or their equivalents, of FSH-α, and Asn-7, or its equivalent, of FSH-β are maintained. In some embodiments, the recombinant FSH-α and FSH-β subunits of the inventive concept may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, or up to 20 amino acid additions, for example, amino acid additions to the N-terminal and/or the C-terminal of a recombinant FSH-α and FSH-β subunit comprising the sequence of SEQ ID NO:1 or SEQ ID NO:2, or may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid additions, for example, amino acid additions to the N-terminal and/or the C-terminal of a FSH-β subunit including a sequence having 90%, 91%, 92%, 93%, 94%, 95%, 96%, 97%, 98%, or 99% sequence identity to SEQ ID NO:2. In some embodiments of the present inventive concept, the recombinant hypo-glycosylated form of FSH includes glycans attached at Asn-52 and Asn-78 of the mature form of FSH-α, for example, as set forth in SEQ ID NO:1, and a glycan attached at Asn-7 of the mature form of FSH-β, for example, as set forth in SEQ ID NO:2. This hypo-glycosylated form of FSH is also known as FSH$^{21}$, and is not glycosylated at Asn-24. In other embodiments, hypo-glycosylated form of FSH includes glycans attached at Asn-52 and Asn-78 of the mature form of FSH-α, for example, as set forth in SEQ ID NO:1, and a glycan attached at Asn-24 of the mature form of FSH-β, for example, as set forth in SEQ ID NO:2. This hypo-glycosylated form of FSH is also known as FSH$^{18}$, and is not glycosylated at Asn-7.

In some embodiments of the present inventive concept, the recombinant hypo-glycosylated form of FSH includes a mature form of FSH-β having and/or including an amino acid sequence as set forth in SEQ ID NO:3, wherein Asn-24 of the mature form of FSH-β (Asn-42 of GenBank/NCBI Accession No. NP_000501.1 or AAA52476.1) is replaced with an Alanine (Ala, N24A), or having and/or including an amino acid sequence as set forth in SEQ ID NO:4, wherein Asn-24 of the mature form of FSH-β is replaced with an Glutamine (Gln, N24Q), either of which amino acid substitution replaces the N-glycosylation site at amino acid position 24 (Asn-24) of these modified forms of the FSH beta-subunit with an amino acid that is not naturally glycosylated, i.e., an amino acid at which a glycan is not and/or cannot be attached through any of the typical glycosylation processes that naturally occur, e.g., N-glycosylation, O-glycosylation, phosphoserine glycosylation, C-mannosylation, and glypiation. As such, since N-glycosylation only takes place at Asn-7 and does not take place at amino acid position 24 of these modified recombinant FSH-β subunits, only FSH$^{21}$ is produced by systems/cells expressing these modified recombinant FSH-β subunits. In some embodiments, the mature form of the modified recombinant FSH-β is encoded for by, for example, nucleotides 55-387 of the sequence as set forth in SEQ ID NO:5. In some embodiments, the modified recombinant FSH-β of the inventive concept is encoded by, for example, a nucleic acid including the sequence as set forth in SEQ ID NO:5. In some embodiments, the mature form of the modified recombinant FSH-β is encoded by nucleotides 55-387 of SEQ ID NO:5. The nucleic acid may further include a heterologous promoter. In some embodiments, the nucleic acid may be part of a vector or expression vector including the sequence as set forth by nucleotides 55-387 of SEQ ID NO:5, i.e., the nucleic acid sequence as set forth in SEQ ID NO:6. In some embodiments, the nucleic acid may be part of a vector or expression vector including the sequence as set forth in SEQ ID NO:5.

```
                                         (SEQ ID NO: 3)
NSCELTNITI AIEKEECRFC ISIATTWCAG YCYTRDLVYK

DPARPKIQKT CTFKELVYET VRVPGCAHHA DSLYTYPVAT

QCHCGKCDSD STDCTVRGLG PSYCSFGEMK E.

                                         (SEQ ID NO: 4)
NSCELTNITI AIEKEECRFC ISIQTTWCAG YCYTRDLVYK

DPARPKIQKT CTFKELVYET VRVPGCAHHA DSLYTYPVAT

QCHCGKCDSD STDCTVRGLG PSYCSFGEMK E.
```

-continued (SEQ ID NO: 5)

```
ATG AAG ACA CTC CAG TTT TTC TTC CTT TTC TGT
TGC TGG AAA GCA ATC TGC TGC AAT AGC TGT GAG
CTG ACC AAC ATC ACC ATT GCA ATA GAG AAA GAA
GAA TGT CGT TTC TGC ATA AGC ATC CAG ACC ACT
TGG TGT GCT GGC TAC TGC TAC ACC AGG GAT CTG
GTG TAT AAG GAC CCA GCC AGG CCC AAA ATC CAG
AAA ACA TGT ACC TTC AAG GAA CTG GTA TAC GAA
ACA GTG AGA GTG CCC GGC TGT GCT CAC CAT GCA
GAT TCC TTG TAT ACA TAC CCA GTG GCC ACC CAG
TGT CAC TGT GGC AAG TGT GAC AGC GAC AGC ACT
GAT TGT ACT GTG CGA GGC CTG GGG CCC AGC TAC
TGC TCC TTT GGT GAA ATG AAA GAA TAA
```

(SEQ ID NO: 6)

```
AAT AGC TGT GAG CTG ACC AAC ATC ACC ATT GCA
ATA GAG AAA GAA GAA TGT CGT TTC TGC ATA AGC
ATC CAG ACC ACT TGG TGT GCT GGC TAC TGC TAC
ACC AGG GAT CTG GTG TAT AAG GAC CCA GCC AGG
CCC AAA ATC CAG AAA ACA TGT ACC TTC AAG GAA
CTG GTA TAC GAA ACA GTG AGA GTG CCC GGC TGT
GCT CAC CAT GCA GAT TCC TTG TAT ACA TAC CCA
GTG GCC ACC CAG TGT CAC TGT GGC AAG TGT GAC
AGC GAC AGC ACT GAT TGT ACT GTG CGA GGC CTG
GGG CCC AGC TAC TGC TCC TTT GGT GAA ATG AAA
GAA
```

In some embodiments, the recombinant FSH-β subunit of the inventive concept may have about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3 or SEQ ID NO:4, e.g., 1, 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid substitutions, additions and/or deletions on one or both subunits, so long as Asn-7, or its equivalent, of FSH-β are maintained, and Ala-24, or its equivalent, of SEQ ID NO:3, or Gln-24, or its equivalent, of SEQ ID NO:4, is not replaced with an amino acid that may be glycosylated. In some embodiments, the recombinant FSH-β subunit of the inventive concept, encoded by, for example, a nucleic acid including a sequence as set forth by SEQ ID NO:5 or SEQ ID NO:6, may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid additions, for example, amino acid additions to the N-terminal and/or the C-terminal of a recombinant FSH-β subunit including a sequence of SEQ ID NO:3 or SEQ ID NO:4, or may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid additions, for example, amino acid additions to the N-terminal and/or the C-terminal of a recombinant FSH-β subunit including a sequence having about 90%, 91%, 92%, 93%, 94%, 95%, 96%, 97%, 98%, or 99% sequence identity to SEQ ID NO:3 or SEQ ID NO:4.

In other embodiments of the present inventive concept, the recombinant hypo-glycosylated form of FSH includes a mature form of FSH-β having an amino acid sequence as set forth in SEQ ID NO:7, wherein Asn-7 of the mature form of FSH-β (Asn-25 of GenBank/NCBI Accession No. NP_000501.1 or AAA52476.1) is replaced with an Alanine (Ala, N7A), or having an amino acid sequence as set forth in SEQ ID NO:8, wherein Asn-7 of the mature form of FSH-β is replaced with an Glutamine (Gln, N7Q), either of which amino acid substitution replaces the N-glycosylation site at amino acid position 7 (Asn-7) of these modified forms of the FSH beta-subunit with an amino acid that is not naturally glycosylated, i.e., an amino acid at which a glycan is not and/or cannot be attached through any of the typical glycosylation processes that naturally occur, e.g., N-glycosylation, O-glycosylation, phosphoserine glycosylation, C-mannosylation, and glypiation. As such, since N-glycosylation only takes place at Asn-24 and does not take place at amino acid position 7 of these modified recombinant FSH-β subunits, only $FSH^{18}$ is produced by systems/cells expressing these modified recombinant FSH-β subunits. In some embodiments, the modified recombinant FSH-β of the inventive concept is encoded by, for example, a nucleic acid including the sequence as set forth in SEQ ID NO:9. In some embodiments, the mature form of the modified recombinant FSH-β is encoded by nucleotides 55-387 of SEQ ID NO:9. The nucleic acid may further include a heterologous promoter. In some embodiments, the nucleic acid may be part of a vector or expression vector including the sequence as set forth by nucleotides 55-387 of SEQ ID NO:9, i.e., the nucleic acid sequence as set forth in SEQ ID NO:10. In some embodiments, the nucleic acid may be part of a vector or expression vector including the sequence as set forth in SEQ ID NO:9.

(SEQ ID NO: 7)

```
NSCELTAITI AIEKEECRFC ISINTTWCAG YCYTRDLVYK
DPARPKIQKT CTFKELVYET VRVPGCAHHA DSLYTYPVAT
QCHCGKCDSD STDCTVRGLG PSYCSFGEMK E.
```

(SEQ ID NO: 8)

```
NSCELTQITI AIEKEECRFC ISINTTWCAG YCYTRDLVYK
DPARPKIQKT CTFKELVYET VRVPGCAHHA DSLYTYPVAT
QCHCGKCDSD STDCTVRGLG PSYCSFGEMK E.
```

(SEQ ID NO: 9)

```
ATG AAG ACA CTC CAG TTT TTC TTC CTT TTC TGT
TGC TGG AAA GCA ATC TGC TGC AAT AGC TGT GAG
CTG ACC CAG ATC ACC ATT GCA ATA GAG AAA GAA
GAA TGT CGT TTC TGC ATA AGC ATC AAC ACC ACT
TGG TGT GCT GGC TAC TGC TAC ACC AGG GAT CTG
```

-continued

```
GTG TAT AAG GAC CCA GCC AGG CCC AAA ATC CAG

AAA ACA TGT ACC TTC AAG GAA CTG GTA TAC GAA

ACA GTG AGA GTG CCC GGC TGT GCT CAC CAT GCA

GAT TCC TTG TAT ACA TAC CCA GTG GCC ACC CAG

TGT CAC TGT GGC AAG TGT GAC AGC GAC AGC ACT

GAT TGT ACT GTG CGA GGC CTG GGG CCC AGC TAC

TGC TCC TTT GGT GAA ATG AAA GAA TAA
```

(SEQ ID NO: 10)

```
AAT AGC TGT GAG CTG ACC CAG ATC ACC ATT GCA

ATA GAG AAA GAA GAA TGT CGT TTC TGC ATA AGC

ATC AAC ACC ACT TGG TGT GCT GGC TAC TGC TAC

ACC AGG GAT CTG GTG TAT AAG GAC CCA GCC AGG

CCC AAA ATC CAG AAA ACA TGT ACC TTC AAG GAA

CTG GTA TAC GAA ACA GTG AGA GTG CCC GGC TGT

GCT CAC CAT GCA GAT TCC TTG TAT ACA TAC CCA

GTG GCC ACC CAG TGT CAC TGT GGC AAG TGT GAC

AGC GAC AGC ACT GAT TGT ACT GTG CGA GGC CTG

GGG CCC AGC TAC TGC TCC TTT GGT GAA ATG AAA

GAA
```

In some embodiments, the recombinant FSH-β subunit of the inventive concept may have about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:7 or SEQ ID NO:8, e.g., 1, 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid substitutions, additions and/or deletions on one or both subunits, so long as Asn-24, or its equivalent, of FSH-β are maintained, and Ala-7, or its equivalent, of SEQ ID NO:7, or Gln-7, or its equivalent, of SEQ ID NO:8, is not replaced with an amino acid that may be glycosylated. In some embodiments, the recombinant FSH-α and FSH-β subunits of the inventive concept, encoded by, for example, a nucleic acid including a sequence as set forth by SEQ ID NO:9 or SEQ ID NO:10, may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid additions, for example, amino acid additions to the N-terminal and/or the C-terminal of a recombinant FSH-α and FSH-β subunit including the sequence of SEQ ID NO:7 or SEQ ID NO:8, or a recombinant FSH-α and FSH-β subunit may include 1 or 2, up to 3, up to 4, up to 5, up to 6, up to 7, up to 8, up to 9, up to 10, up to 11, up to 12, up to 13, up to 14, up to 15, up to 16, up to 17, up to 18, up to 19, up to 20, up to 21, up to 22, up to 23, up to 24, up to 25, up to 26, up to 27, up to 28, up to 29, or up to 30 amino acid additions, for example, amino acid additions to the N-terminal and/or the C-terminal of a sequence having 90%, 91%, 92%, 93%, 94%, 95%, 96%, 97%, 98%, or 99% sequence identity to SEQ ID NO:7 or SEQ ID NO:8.

Preparation of the recombinant hypo-glycosylated form of FSH include any recombinant methods that would be appreciated by one of skill in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York). Although the recombinant hypo-glycosylated form of FSH may be produced in any cell line, in some embodiments, FSH, recombinant FSH and/or recombinant hypo-glycosylated FSH of the inventive concept is a human FSH is obtained/derived from human or mammalian cells, and in some embodiments, obtained/derived from a human or mammalian cell line. Human cell lines used to produce recombinant FSH of the inventive concept may include, for example, GT-5s, or Per.C6. In some embodiments, recombinant FSH, such as the hypo-glycosylated form of FSH of the inventive concept, is produced in a cell line derived from the pituitary gland, such as the cell line GH3, derived from a rat pituitary tumor. In other embodiments, the recombinant FSH of the inventive concept may be expressed and produced and isolated from non-mammalian cell line, for example, insect cells in which a baculovirus expression vector system may be used, such as, but not limited to, for example, BTI-Tn-5B1-4 (High Five or Hi5) cells.

It will also be appreciated that glycan structures that may be included at the glycosylation sites on the FSH and recombinant FSH of the inventive concept are not particularly limited. Sugars that are part of the glycan structure may include, for example, fructose, galactose, mannose, galactosamine, glucosamine, and/or sialic acid. Nonetheless, in some embodiments, it will be appreciated that the FSH and recombinant FSH of the inventive concept will include glycan structures, for example, a glycan/sugar structure at Asn-52 and/or Asn-78 of human FSH-α, or their equivalents, and a glycan/sugar structure at Asn-7 and/or at Asn-24 of human FSH-β, or their equivalents, that will be identical to or substantially identical to the glycan structures of FSH produced in the pituitary gland of a human or mammalian body/subject.

According to further embodiments of the present inventive concept, provided are pharmaceutical compositions including a therapeutically effective amount of the recombinant hypo-glycosylated form of FSH. In some embodiments, the pharmaceutical composition further comprises a pharmaceutically acceptable carrier. The term "pharmaceutically acceptable carrier" as used herein refers to any substance, not itself a therapeutic agent, used as at least in part a vehicle for delivery of a therapeutic agent to a subject. Non-limiting examples of pharmaceutically acceptable components include, without limitation, any of the standard pharmaceutical carriers such as phosphate buffered saline solutions, water, emulsions such as oil/water emulsions or water/oil emulsions, microemulsions, and various types of wetting agents. Further, in preparing such pharmaceutical compositions comprising the active ingredient or ingredients in admixture with components necessary for the formulation of the compositions, other conventional pharmacologically acceptable additives may be incorporated, for example, excipients, stabilizers, wetting agents, emulsifying agents, lubricants, sweetening agents, coloring agents, flavoring agents, isotonicity agents, buffering agents, antioxidants and the like. Additives may include, for example, starch, mannitol, sorbitol, precipitated calcium carbonate, crystalline cellulose, carboxymethylcellulose, dextrin, gelatin, acacia, EDTA, magnesium stearate, talc, hydroxypropylmethylcellulose, sodium metabisulfite, and the like.

Formulations suitable for administering the composition of the present inventive concept may be suitable for any route of administration as would be appreciated by one of skill in the art. Routes of administration may include, but are not limited to intravenous, oral, parenteral, subcutaneous, topical and/or vaginal methods of administration.

Methods of Administration

Another embodiment of the present inventive concept provides a method for administering to a subject in need thereof a compound or pharmaceutical composition as described herein. For administration, either the compound or pharmaceutical composition is understood as being the active ingredient and capable of administration to a subject, and thus, in some instances, the terms are interchangeable.

The method of administration of the compound or pharmaceutical composition as described herein is not particularly limited, and any method that would be appreciated by one of skill in the art for the compound or pharmaceutical composition in a particular formulation as described herein. Routes of administration may include, but are not limited to intravenous, oral, parenteral, subcutaneous, topical and/or vaginal methods of administration.

Subjects suitable to be treated with the composition, compositions and formulations of the present invention include, but are not limited to mammalian subjects. Mammals according to the present invention include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment according to the present invention is suitable. In some embodiments of the present inventive concept, the subject is a human subject. Although the human subject treated according to methods of the present inventive concept may be of any gender (for example, male, female or transgender) and at any stage of development (i.e., neonate, infant, juvenile, adolescent, adult, elderly), in some embodiments, the human subject is a premenopausal, menopausal, or postmenopausal female human subject.

Dosages of compositions and formulations of the present inventive concept may depend on route of administration and intended use. It will be appreciated by one of skill in the art that international units (IU) for FSH may refer to the fourth International Standard for human urinary FSH (Stoning and Gaines Das 2001, *J. Endocrinol.* 171, 119-129), determined as described by Steelman and Pohley 1953, *Endocrinol.* 53, 604-616. For example, 450 IU of FSH, corresponds to 33 mcg of FSH (41 IU corresponds to 3 mcg, ~13.67 IU/mcg). Typical dosages available of commercially available FSH, such as GONAL-F®, GONAL-F RFF®, FOLLISTIM AQ®, and PUREGON®, may be in a range of about 1-10,000 IU, 10-3,600 IU and/or 37.5-1,200 IU, and include dosages of, for example, 37.5 IU, 75 IU, 150 IU, 300 IU, 450 IU, 600 IU, 750 IU, 900 IU, 1,050 IU, and 1,200 IU, which may be provided as a solid for dissolving in a carrier for administration, such as subcutaneous administration, or provided as a solution in, for example, 0.75 mL or 1.0 mL volume of a suitable carrier for subcutaneous administration/injection. Dosages and dosing regimens of FSH compositions are known, and any dosage and dosing regimens for FSH compositions and formulations may be used for the FSH compositions and formulations of the present inventive concept. Known dosing regimens include, for example, daily subcutaneous administration, initially for 5 days, 7 days or 14 days, with duration of therapy running until response is achieved.

Uses

Methods of use of compounds, compositions and formulations of the present inventive concept include methods for treatment or prevention of a number of medical conditions, including, for example, methods of treating infertility, methods of inducing oocyte/egg growth and/or maturation, methods of stimulating sex steroid secretion, methods for treating and/or preventing the loss of bone density, for example, such as the loss of bone density as a result of osteoporosis, and methods for treating and/or preventing fatty tissue accumulation, for example, such as fatty tissue accumulation associated with the onset of menopause, in a subject in need thereof.

Treating infertility, or infertility treatment, according to embodiments of the inventive concept include treatment of a dysfunction, disorder, or disease related to reproduction or fertility in a human or non-human (animal) subject including administration of compositions and/or formulations of the inventive concept as described herein. In some embodiments, treating infertility includes assisted reproductive technologies (ART), including but not limited to in vitro fertilization, in vitro fertilization with intracytoplasmic sperm injection, ovulation induction, and ovulation induction with intrauterine insemination. In some embodiments, treating infertility includes treatment of ovulatory disorders, treatment of disorders related to egg maturation, as well as inducing, enabling and/or improving folliculogenesis and/or spermatogenesis, inducing, enabling and/or improving Sertoli cell proliferation, and treating hypogonadotropic hypogonadism in the subject.

In some embodiments, treating infertility according to the inventive concept may include methods of inducing and/or stimulating secretion/production of sex steroids in the subject including administration of compositions and/or formulations of the inventive concept as described herein. Sex steroids, or sex hormones, refer to steroid hormones that interact with androgen or estrogen receptors. Sex steroids include: androgens, e.g., anabolic steroids, androstenedione, dehydroepiandrosterone, dihydrotestosterone and testosterone; estrogens, e.g., estradiol, estriol and estrone; and progesterone. In some embodiments, inducing and/or stimulating secretion/production of sex steroids include inducing and/or stimulating secretion/production of estrogens, for example, estradiol, and/or inducing and/or stimulating secretion/production progesterone.

In some embodiments, treating infertility according to the inventive concept may include induction of follicle growth and/or maturation including administration of compositions and/or formulations of the inventive concept as described herein. In some embodiments, treating infertility may include induction of oocyte/egg growth and/or maturation including administration of compositions and/or formulations of the inventive concept as described herein.

In some embodiments, treating infertility according to the inventive concept may include inducing, enabling and/or improving Sertoli cell proliferation including administration of compositions and/or formulations of the inventive concept as described herein. In some embodiments, treating infertility may include treating hypogonadotropic hypogonadism including administration of compositions and/or formulations of the inventive concept as described herein.

Treating and/or preventing loss of bone density according to embodiments of the inventive concept may include treating and/or preventing conditions and diseases including administration of compositions and/or formulations of the inventive concept as described herein to a subject in which the inhibition of bone loss and/or the promotion of bone formation is desirable. Such conditions and diseases include, for example, osteoporosis, osteomyelitis, Paget's disease, periodontitis, hypercalcemia, osteonecrosis, osteosarcoma, osteolyic metastases, familial expansile osteolysis, prosthetic loosening, periprostetic osteolysis, cleiodocranial dysplasia (CCD), osteoporosis from arthritides, and bone loss due to metastatic disease and humoral hypercalcemia. In some embodiments, treating and/or preventing loss of bone density includes methods of treating and/or preventing osteoporosis in a subject. In some embodiments, treating and/or preventing loss of bone density includes treating a human subject. In some embodiments, the human subject is a female human subject. In some embodiments, the female human subject. In some embodiments, the female human subject may be premenopausal. In some embodiments, the female human subject may be perimenopausal. In some embodiments, the female subject may be postmenopausal, or in menopause.

Treating and/or preventing fatty tissue accumulation according to embodiments of the inventive concept may include administration of compositions and/or formulations of the inventive concept as described herein to treat and/or prevent fatty tissue accumulation that may result from, for example, a female subject, such as a female human subject approaching or entering menopause, e.g., a perimenopausal female human subject, or treating and/or preventing fatty tissue accumulation in a female human subject that is in menopause, but is not limited thereto.

The present invention is more particularly described in the following examples, which is intended to be illustrative only, since numerous modifications and variations therein will be apparent to those skilled in the art.

EXAMPLES

1. Recombinant Hypo-Glycosylated $FSH^{21}$

Hypo-glycosylated $FSH^{21}$ contains one N-linked sugar chain attached to the $Asn^7$ residue of the human FSH-β subunit. Current commercially available FSH preparations include predominantly fully glycosylated $FSH^{24}$, in which glycan structures are present on both $Asn^7$ and $Asn^{24}$ residues of the FSH-β subunit. The product developed is a recombinant human $FSH^{21}$ expressed in GH3 cells derived from a rat pituitary gland tumor. The recombinant $FSH^{21}$ produced in GH3 cells has been modified by site-directed mutagenesis, substituting $Asn^{24}$ with Alanine, thus eliminating the $Asn^{24}$ glycosylation site, and as such the recombinant FSH produced in this GH3 cell genomic clone is a recombinant $FSH^{21}$, glycosylated at $Asn^{52}$ and $Asn^{78}$ of FSH-α, and only at $Asn^7$ of FSH-β.

Figure 1B:
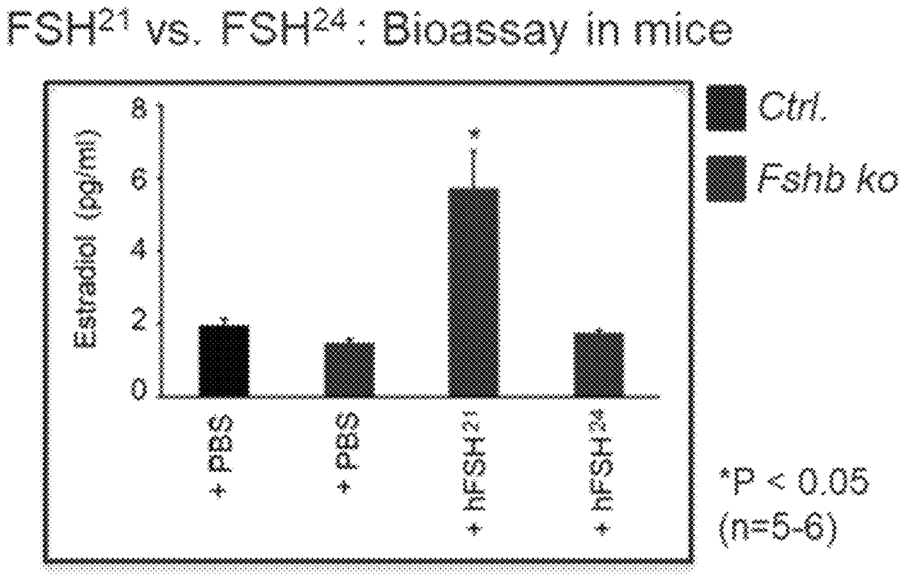

Induction of estradiol and progesterone production by this recombinant $FSH^{21}$ was compared to $FSH^{24}$ in vitro in a human ovary KGN granulosa cell line, and induction of estradiol production by this recombinant $FSH^{21}$ was compared to $FSH^{24}$ in vivo by administration to Fshb knockout mice. The results of this examination are shown in FIGS. 1A and 1B. The in vitro studies show that this recombinant $FSH^{21}$ is more effective at inducing both estradiol and progesterone production than full-glycosylated $FSH^{24}$ at all FSH concentrations from 1-100 ng/ml (FIG. 1A). The in vivo studies show administration of this recombinant $FSH^{21}$ is superior to administration of fully-glycosylated $FSH^{24}$ at inducing estradiol production in Fshb knockout mice (FIG. 1B).

Figure 2:
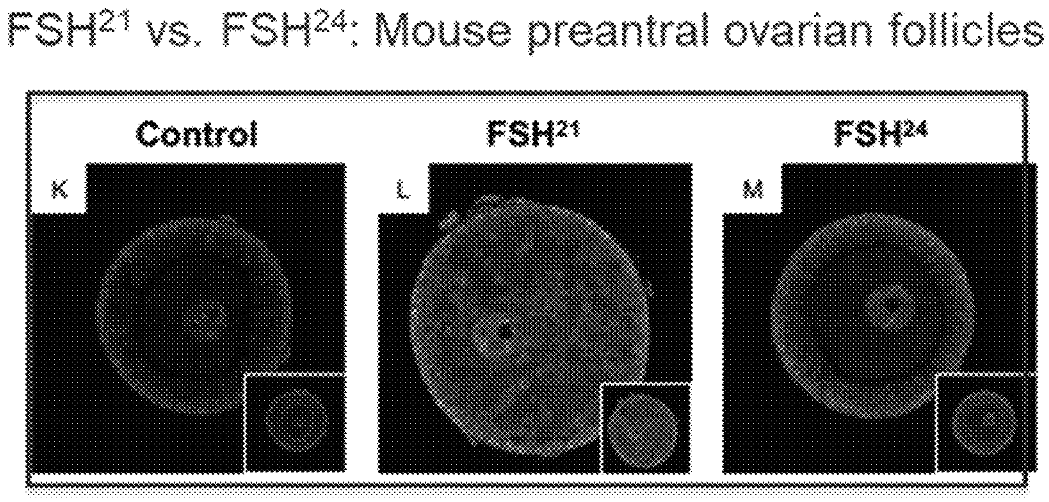
FIG. 2 depicts the comparison of preantral ovarian follicle induction by recombinant $FSH^{21}$ and fully-glycosylated $FSH^{24}$.

Induction of preantral ovarian follicle growth by this recombinant $FSH^{21}$ was compared to $FSH^{24}$, and the results of this examination are shown in FIG. 2. These results show that this recombinant $FSH^{21}$ is more effective at inducing gene expression in preantral ovarian follicle production than full-glycosylated $FSH^{24}$.

Figure 3A:
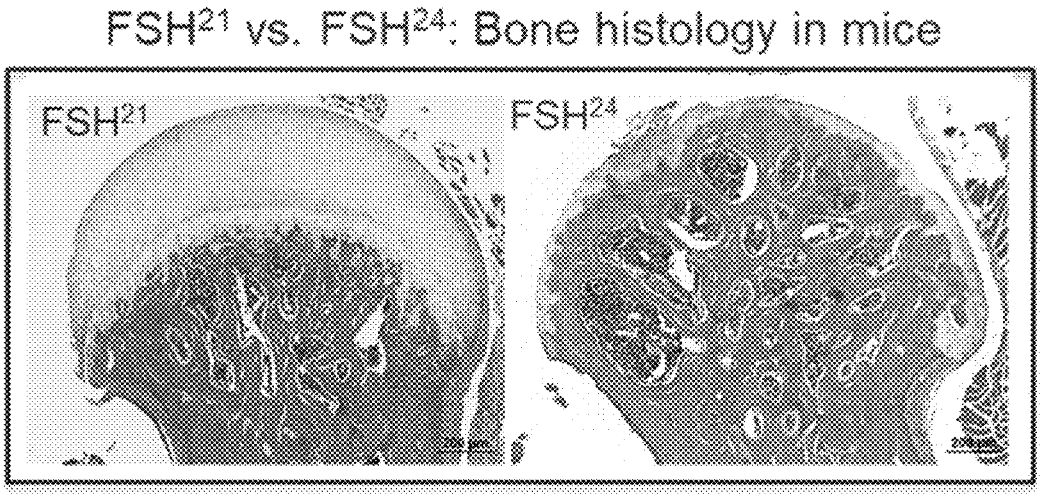
FIGS. 3A and 3B depict the comparison of bone health histologically (FIG. 3A) and by CT imaging (FIG. 3B) of mice expressing recombinant $FSH^{21}$ and fully-glycosylated $FSH^{24}$.
Figure 3B:
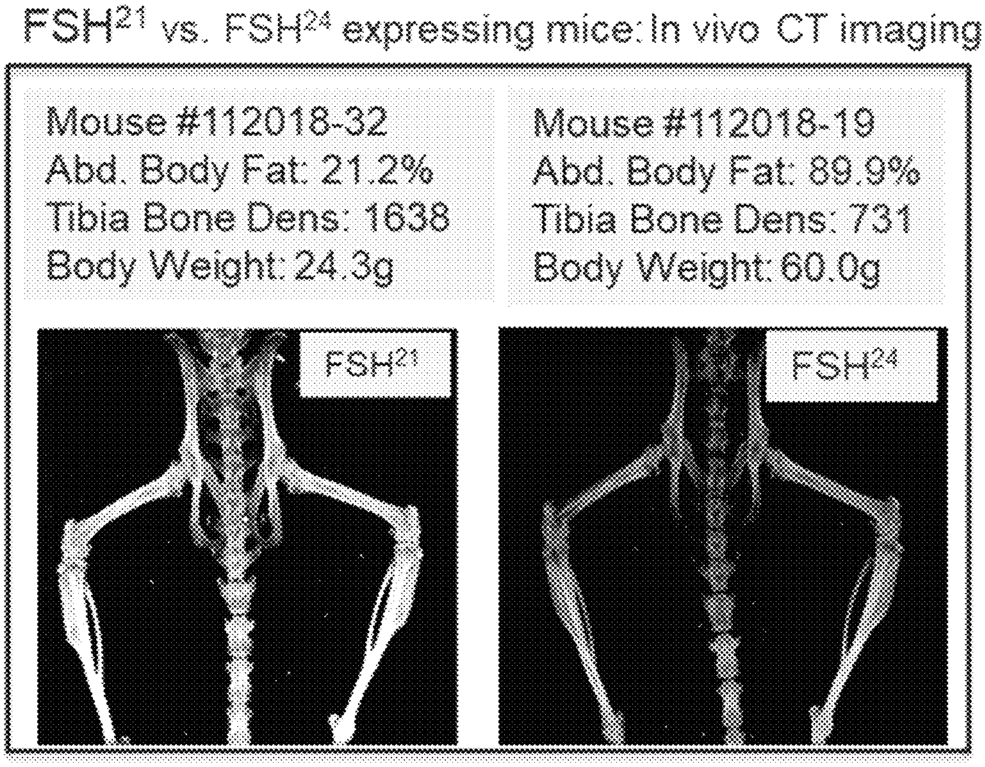

Bone health in mice expressing this recombinant $FSH^{21}$ was compared to mice expressing $FSH^{24}$, and the results of this examination are shown in FIGS. 3A and 3B. Histological examination by hematoxylin and eosin staining (FIG. 3A) and CT imaging (FIG. 3B) both show mice expressing this recombinant $FSH^{21}$ exhibit greater bone density than mice expressing full-glycosylated $FSH^{24}$.

2. Bone Quality in Mice Expressing Hypo-Glycosylated FSH Compared to Fully Glycosylated FSH Generation of $FSH\beta^{21}$ and $FSH\beta^{18}$ expressing mice: The human FSHB wild-type gene (encodes $FSH\beta^{24}$) was separately PCR mutagenized at nucleotides coding for $Asn^{24}$ (codes for $FSH\beta^{21}$) and $Asn^7$ (codes for $FSH\beta^{18}$). The purified transgene DNA fragments were separately microinjected into one-cell mouse embryos and transgene founders for produced. After stably propagating the transgene into F2 generation, individual lines were introduced onto Fshb null genetic background to derive $FSH^{24}$, $FSH^{21}$ and $FSH^{18}$ expressing mice.

Figure 4A:
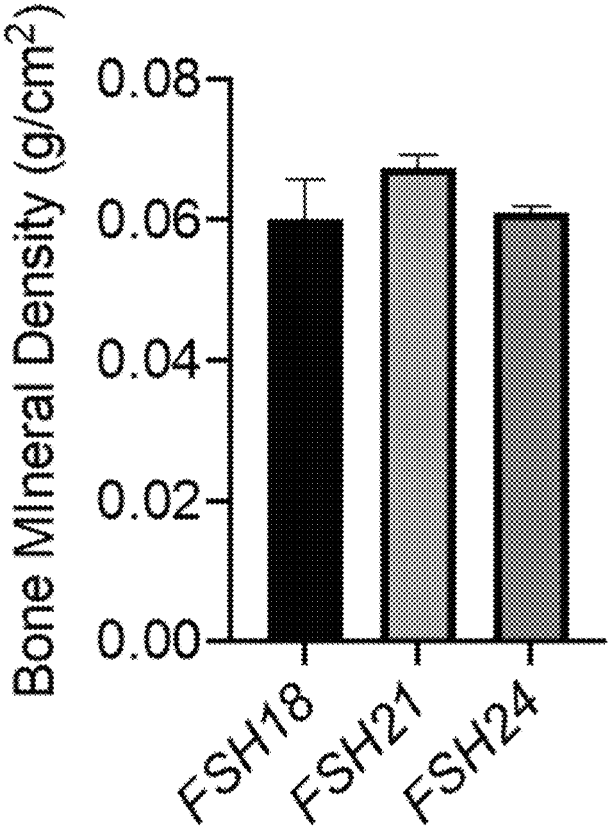
FIGS. 4A and 4B depict in vivo dual-energy X-ray absorptiometry (DEXA, or DXA) examining bone mineral density (FIG. 4A) and content (FIG. 4B) of 8-month old female mice expressing $FSH^{18}$, $FHS^{21}$, or $FSH^{24}$ glycoforms.
Figure 4B:
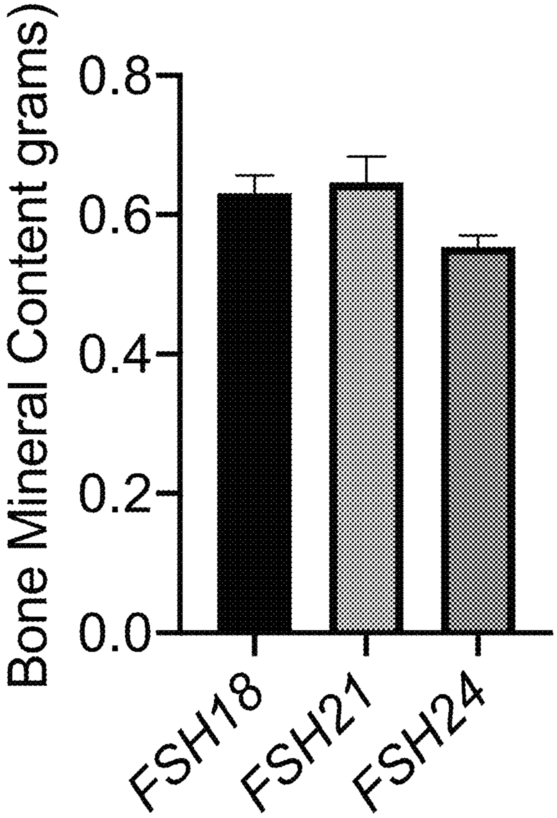

Bone mineral density and content of female mice expressing $FSH^{18}$, $FHS^{21}$, or $FSH^{24}$ glycoforms was examined at 8 months of age (N=11-17) using in vivo dual-energy X-ray absorptiometry (DEXA, or DXA). The results of this examination are shown for bone mineral density in FIG. 4A and bone mineral content in FIG. 4B. These results indicate that mice expressing $FSH^{21}$ and $FSH^{18}$, hypo-glycosylated forms of FSH-β, particularly mice expressing $FSH^{21}$, exhibit higher bone mineral density and bone mineral content ($P<0.05$) than mice expressing fully glycosylated ($FSH^{24}$) forms of FSH-β.

Figure 5A:
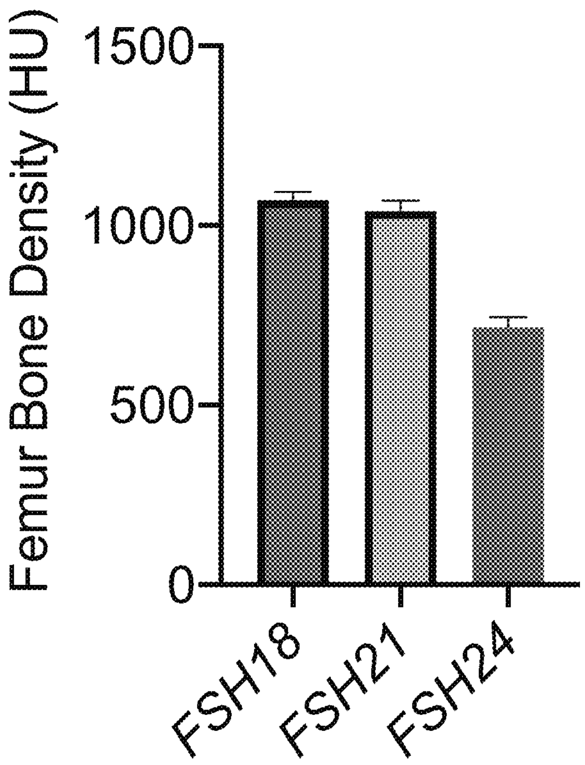
FIGS. 5A and 5B depict in vivo X-ray computed tomography (CT) analysis of bone density of the femur (FIG. 5A) and tibia (FIG. 5B) of 8-month old female mice expressing $FSH^{18}$, $FHS^{21}$, or $FSH^{24}$ glycoforms.
Figure 5B:
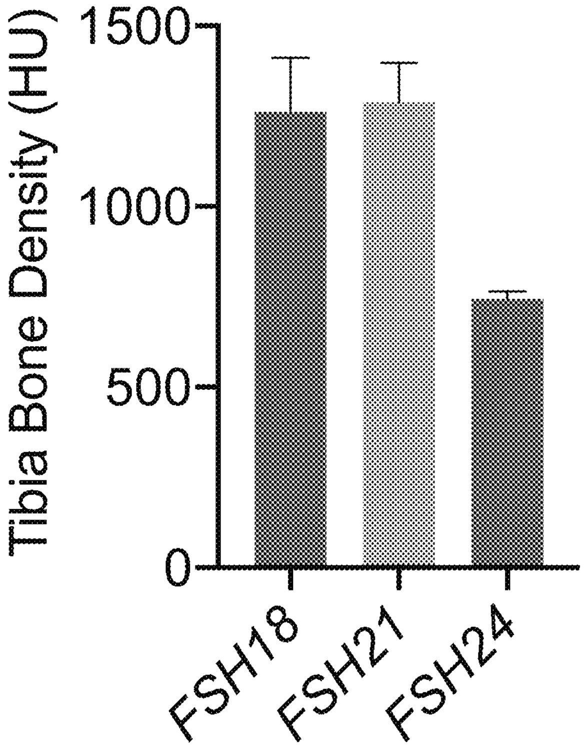

Bone density of the femur and tibia of female mice expressing $FSH^{18}$, $FHS^{21}$, or $FSH^{24}$ glycoforms was examined at 8 months of age (N=3-7) using in vivo X-ray computed tomography (CT) analysis. The results of this examination are shown in FIGS. 5A and 5B. These results indicate that mice expressing $FSH^{21}$ and $FSH^{18}$, hypo-glycosylated forms of FSH-β, exhibit higher bone density in both the femur (FIG. 5A) and tibia (FIG. 5B) ($P<0.05$) than mice expressing fully-glycosylated ($FSH^{24}$) forms of FSH-β.

Figure 6:
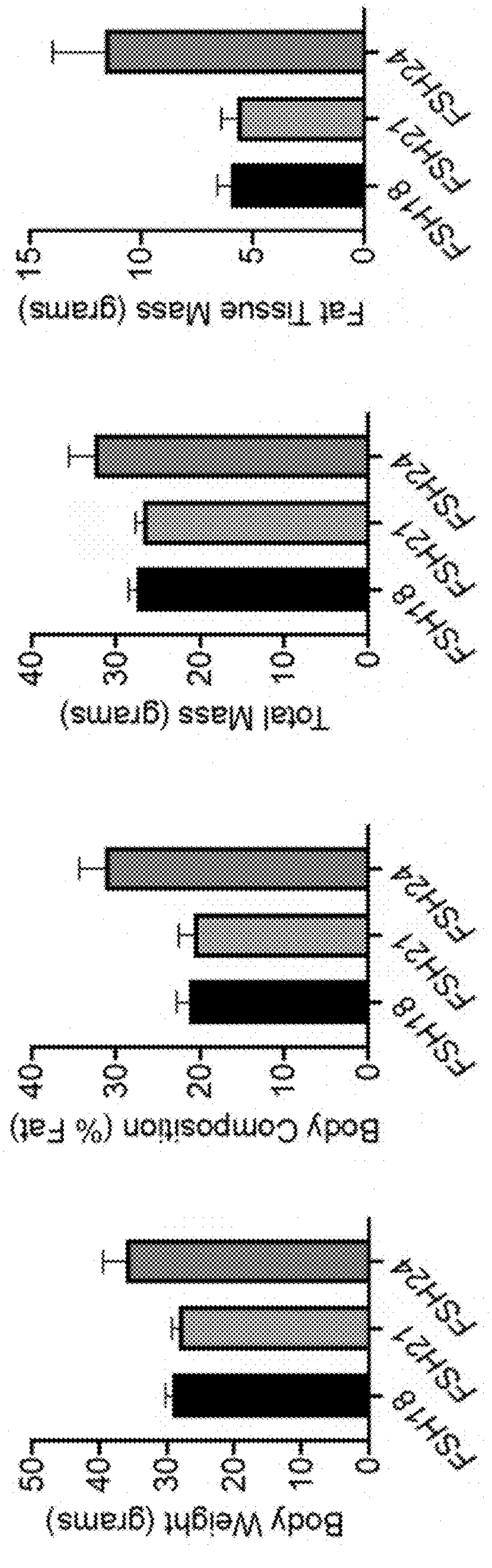
FIG. 6 depicts in vivo DEXA examining body weight, percent body fat composition, total mass, and total fat tissue mass of 8-month old female mice expressing $FSH^{18}$, $FHS^{21}$, or $FSH^{24}$ glycoforms.

3. Fat Accumulation in Mice Expressing Hypo-Glycosylated FSH Compared to Fully Glycosylated FSH Body weight, fat composition, total mass and fatty tissue mass of female mice expressing $FSH^{18}$, $FHS^{21}$, or $FSH^{24}$ glycoforms was examined at 8 months of age (N=11-17) using in vivo DEXA. The results of this examination are shown in FIG. 6. These results indicate that mice expressing $FSH^{21}$ and $FSH^{18}$, hypo-glycosylated forms of FSH-β, exhibit lower body weight, fat composition, indicated by % body weight of fat, total body mass, and total fat mass (P<0.05) than mice expressing fully glycosylated ($FSH^{24}$) forms of FSH-β.

Figure 7:
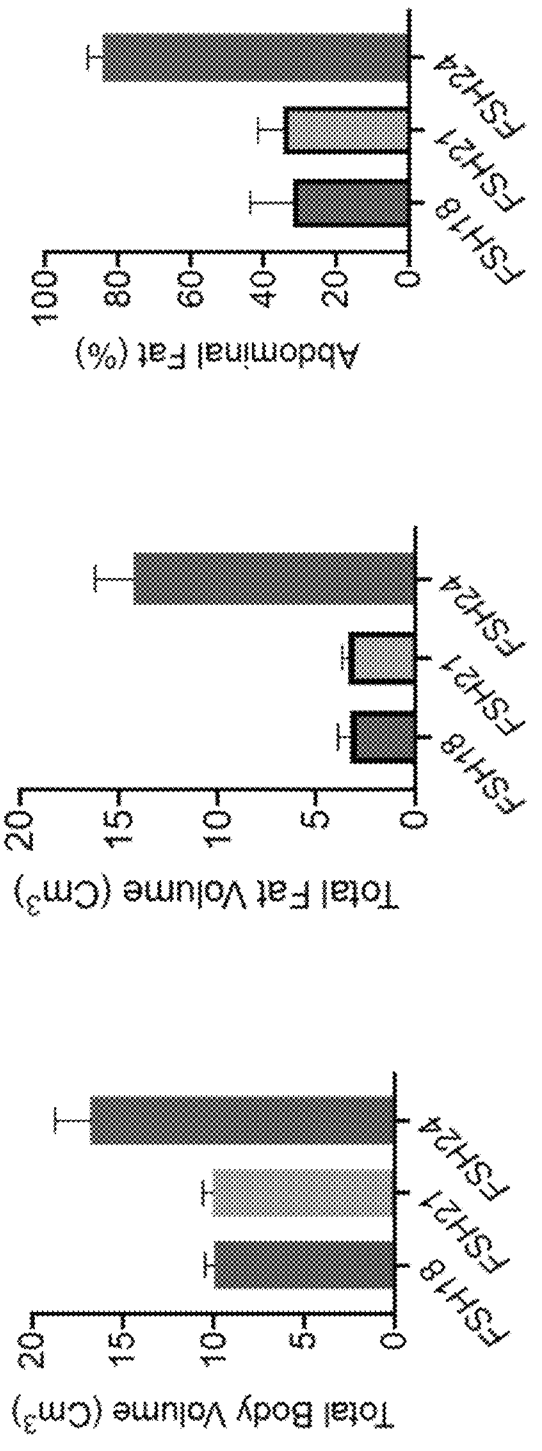
FIG. 7 depicts in vivo MRI analysis examining total body and total fat volume, and abdominal fat percentage of 8-month old female mice expressing $FSH^{18}$, $FHS^{21}$, or $FSH^{24}$ glycoforms.

Total body volume, total fat volume, and abdominal fat percentage of female mice expressing $FSH^{18}$, $FHS^{21}$, or $FSH^{24}$ glycoforms was examined at 8 months of age (N=3-7) using in vivo MRI analysis. The results of this examination are shown in FIG. 7. These results indicate that mice expressing $FSH^{21}$ and $FSH^{18}$, hypo-glycosylated forms of FSH-β, exhibit lower total body volume, total fat volume, and percentage abdominal fat (P<0.05) than mice expressing fully glycosylated (FSH24) forms of FSH-β.

The foregoing is intended to be illustrative of the present invention and is not to be construed as limiting thereof. The invention is defined by the following claims, with equivalents of the claims to be included therein.

That which is claimed is:

1. A method of inducing follicle growth and/or maturation in a subject in need thereof, wherein the method comprises administering to the subject a therapeutically effective amount of a modified recombinant follicle-stimulating hormone (rFSH), and wherein the modified rFSH comprises a modified recombinant FSH beta-subunit (rFSHβ) comprising the amino acid sequence of SEQ ID NO: 4.

2. The method of claim 1, wherein the inducing follicle growth and/or maturation is for treating infertility in the subject.

3. The method of claim 1, wherein the inducing follicle growth and/or maturation is for inducing oocyte/egg growth and/or maturation in the subject.

4. The method of claim 1, wherein the inducing follicle growth and/or maturation is for stimulating secretion of a sex steroid in the subject.

5. The method of claim 1, wherein the inducing follicle growth and/or maturation is for treating loss of bone density in the subject.

6. The method of claim 1, wherein the inducing follicle growth and/or maturation is for treating fatty tissue accumulation in the subject.

7. The method of claim 1, wherein the subject is a human subject.

8. The method of claim 7, wherein the human subject is a female human subject.

9. The method of claim 1, wherein the modified rFSHβ further comprises an addition of up to 30 amino acids at the N-and/or C-terminal of SEQ ID NO:4.

10. The method of claim 9, wherein the modified rFSHβ comprises an addition of up to 30 amino acids at the C-terminal of SEQ ID NO:4.

11. The method of claim 1, wherein the modified rFSH is administered in a pharmaceutical composition comprising the modified rFSH and a pharmaceutically acceptable carrier.

12. The method of claim 1, wherein the modified rFSH is more effective at inducing follicle growth and/or maturation as compared to fully glycosylated rFSH.

13. The method of claim 12, wherein the more effective follicle growth and/or maturation comprises increased estradiol production as compared to fully glycosylated rFSH.

14. The method of claim 12, wherein the more effective follicle growth and/or maturation comprises increased gene expression in preantral follicles as compared to fully glycosylated rFSH.

* * * * *